(12) United States Patent
Haney et al.

(10) Patent No.: US 7,699,360 B2
(45) Date of Patent: *Apr. 20, 2010

(54) WATER WELL CASING

(76) Inventors: Morris G. Haney, P.O. Box 4457, Beeville, TX (US) 78104; Roy L. Thein, 10816 S. Sooner Rd., Oklahoma City, OK (US) 73165

( * ) Notice: Subject to any disclaimer, the term of this patent is extended or adjusted under 35 U.S.C. 154(b) by 0 days.

This patent is subject to a terminal disclaimer.

(21) Appl. No.: 11/810,168

(22) Filed: Jun. 5, 2007

(65) Prior Publication Data
US 2007/0235183 A1    Oct. 11, 2007

Related U.S. Application Data

(63) Continuation of application No. 10/965,108, filed on Oct. 14, 2004, now Pat. No. 7,249,789.

(51) Int. Cl.
*F16L 21/02* (2006.01)
(52) U.S. Cl. .................... 285/374; 285/332.3; 285/347; 285/921; 138/109
(58) Field of Classification Search ................. 285/319, 285/322, 330, 331, 332.1, 332.2, 332.3, 347, 285/374, 921, 7; 405/251; 403/289, 290
See application file for complete search history.

(56) References Cited

U.S. PATENT DOCUMENTS

| 1,039,354 A |   | 9/1912  | Bonadio |            |
|-------------|---|---------|---------|------------|
| 1,678,280 A |   | 7/1928  | Carson  |            |
| 2,455,544 A | * | 12/1948 | Yonkers | ........... 285/7 |
| 2,537,284 A |   | 1/1951  | Schuder |            |
| 3,413,021 A |   | 11/1968 | Potts   |            |
| 3,784,235 A |   | 1/1974  | Kessler |            |
| 3,837,661 A | * | 9/1974  | Phillippi | ........... 279/131 |
| 3,927,703 A | * | 12/1975 | Beaubien | ........... 141/333 |
| 3,950,014 A | * | 4/1976  | Doubleday | ........... 285/7 |
| 4,030,850 A |   | 6/1977  | Hyde    |            |
| 4,110,144 A | * | 8/1978  | Buehler et al. | ........... 156/173 |
| 4,128,264 A |   | 12/1978 | Oldford |            |
| 4,486,034 A | * | 12/1984 | Sauer   | ........... 285/242 |
| 4,523,780 A |   | 6/1985  | Cheer   |            |
| 4,552,387 A |   | 11/1985 | Schmidt |            |
| 4,779,902 A |   | 10/1988 | Lee     |            |
| 4,803,053 A |   | 2/1989  | Williamson |         |

(Continued)

*Primary Examiner*—James M Hewitt
(74) *Attorney, Agent, or Firm*—Gunn, Lee & Cave, P.C.; John C. Cave

(57) ABSTRACT

A novel design for the connection of lengths of polyvinyl chloride (PVC) casing. Each length of casing has a male end and a female end. The female end has a narrowing interior diameter with its wider interior diameter at its outermost end sufficient to receive the male end of similar length of casing for connection. The diameter of the female end narrows to a diameter which is less than the outer diameter of the male end. The male end has a lip at its leading edge and is slotted and compressible when forced through the narrowed diameter of the female end. A groove in the interior surface of the female end is sufficient to receive the lip at the leading edge of the male end. When the lip at the leading edge of the male end reaches the groove, it allows the compressed male end to expand with the groove receiving the lip therein. The connected lengths of casing are locked together in this manner.

45 Claims, 5 Drawing Sheets

U.S. PATENT DOCUMENTS

| | | |
|---|---|---|
| 4,875,714 A | 10/1989 | Lee |
| 4,887,849 A | 12/1989 | Briet |
| 5,015,014 A | 5/1991 | Sweeney |
| 5,031,266 A * | 7/1991 | Tillman et al. ............. 15/327.2 |
| 5,039,133 A * | 8/1991 | Albrecht ........................ 285/7 |
| 5,255,945 A | 10/1993 | Toon |
| 5,662,360 A | 9/1997 | Guzowski |
| 5,918,914 A | 7/1999 | Morris |
| 6,176,523 B1 | 1/2001 | Winslett |
| 6,499,772 B1 | 12/2002 | Minemyer |
| 6,568,658 B2 | 5/2003 | Strome |
| 2007/0007762 A1 * | 1/2007 | Hull et al. .............. 285/148.23 |

* cited by examiner

WATER WELL CASING

CROSS REFERENCE TO RELATED APPLICATION

This is a continuation application claiming priority to U.S. patent application Ser. No. 10/965,108 filed Oct. 14, 2004 now U.S. Pat. No. 7,249,789.

BACKGROUND OF THE INVENTION

1. Field of the Invention

Applicant's invention relates to a novel design for water well casing for use in water well and related systems.

2. Background Information

In water well systems, a casing is inserted into the well to maintain the structure of the well. Typically, a submersible pump is placed within the well and is attached a drop pipe which carries the water from the well to the surface. Since water well casing must extend many feet into the ground, it is advantageous to manufacture the casing in sections to facilitate installation as well as repair. Generally, these sections are held together with glue or a pipe coupling. Unfortunately, the positioning of couplings can take a great deal of effort to assemble properly and the use of glue is time-consuming as glue requires a "set" time. Therefore, with current practices and materials, well drillers do not have the ability to run the casing into the well by simply and rapidly connecting one section of casing to another.

The present invention was designed to solve this problem. In the preferred embodiment, water well casing sections are provided having both male and female ends. The male end of one length of casing section fits within the female end of another length of casing. The male end is slotted and compressible when forced into the female end. The male end provides a lip which locks into a groove in the interior surface of the female end when the male end is fully inserted. The procedure allows the water well casing to be connected easily and efficiently without the use of glue or couplings.

A patent issued to Potts, U.S. Pat. No. 3,413,021, discloses a similar design for metal tubular couplings. Unlike the present invention, Potts discloses a coupling which is resistant to compressive forces and can be disassembled easily when pulled apart. On the other hand, the present invention is designed to resist the pulling or hanging loads which exist when the casing is placed in the well.

A patent issued to Oldford, U.S. Pat. No. 4,128,264 also has similarities to the present invention. However, the Oldford patent discloses a design for metal fittings to be used with metal pipe as opposed to plastic PVC casing disclosed in the present invention.

The prior art is devoid of any similar designs to be used with plastic piping or casing in water well applications.

SUMMARY OF THE INVENTION

It is an object of the present invention to provide novel water well casing that permits installation and connection without the use of glue or couplings. In satisfaction of these and related objectives, Applicant's present invention provides water well casing having a main length between male and female ends. The main length of the casing has a uniform inner and outer diameter and is contiguous with the male and female ends. The male end has slots which are spaced around the circumference of the casing. The slots extend from the leading edge of the male end in a direction parallel to the length of the casing. The male end also has a lip at its leading edge. The lip is beveled at its front edge and forms a shoulder at its rear edge.

The female end has a first female section with a widened interior diameter at its outermost end designed to receive a male end of a similar length of casing. The interior diameter of the female end tapers and narrows to another section having a diameter which is less than outer diameter of the lip at the male end. A groove in interior surface of the female end is designed to receive and hold the lip of a similar length of casing.

During installation, the male end of one length of casing compresses as it is forced through the tapered diameter of the female end of another length of casing. Once the lip at the leading edge of the male end reaches the groove, the male end expands with the groove receiving and locking the lip therein.

DETAILED DESCRIPTION OF THE PREFERRED EMBODIMENT

Figure 1:
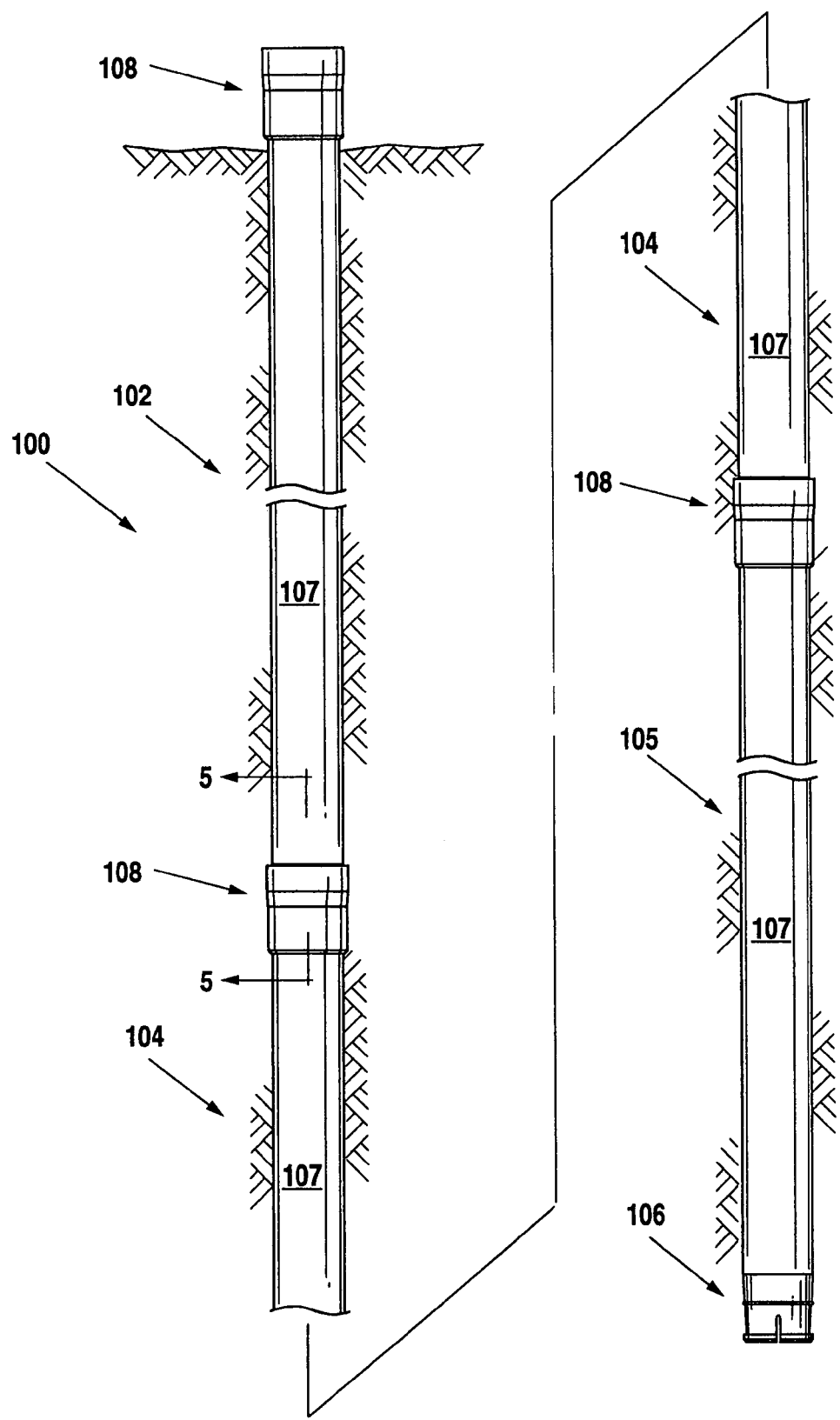
FIG. 1 is a front elevation view of a typical water well casing assembly.

FIG. 1 depicts a water well 100 with casing 102 placed in the water well 100 to maintain the integrity of the well 100 and protect pipe (not shown) within the casing 102. The casing 102 is present in separate similar lengths of casing 104 and 105 and connected one to the next by way of male ends 106 and female ends 108 shown in more detail in FIGS. 2, 3, and 4.

Referring to FIGS. 1, 2, 3, and 4, the casing 102 of the present invention consists of three parts, a main length 107, a male end 106 and a female end 108. In the preferred embodiment, the male end 106 has a tapering section 110 extending from the main length 107 to a lip 112 at the leading edge of the male end 106. The outer diameter of the lip 112 is substantially equal to the outer diameter of the main length 107. However, other designs of the male end are anticipated. For example, the outer diameter at the male end 106 could be uniform and equal to the outer diameter of the main length 107 with the lip 112 having an outer diameter greater than that of the main length 107. In another example, the male end 106 could have a uniform diameter which is narrower than the diameter of the main length.

Preferably, the interior diameter of the male end 106 is equal to the interior diameter of the main length 107. However, it is anticipated that the interior diameter of the male end 106 could be greater or less than the interior diameter of the main length 107.

In the preferred embodiment, the lip 112 has a beveled leading edge 120 and a squared shoulder 121 at its rear edge. However, it is anticipated that other designs for the lip could be utilized. For example, the leading edge of the lip 112 could be squared or rounded and the rear edge of the lip 112 could be curved or angled rearwardly.

The male end 106 has slots 122, which are spaced around the circumference of the male end 106 and extend from the lip 112 into the tapering section 110 in a direction substantially parallel to the length of the casing 102. Preferably, there are a plurality of slots 122 equally spaced around the circumference of the male end 106. However, it is anticipated that as few as one slot or a plurality of nonequally spaced slots could be utilized.

Figure 2:
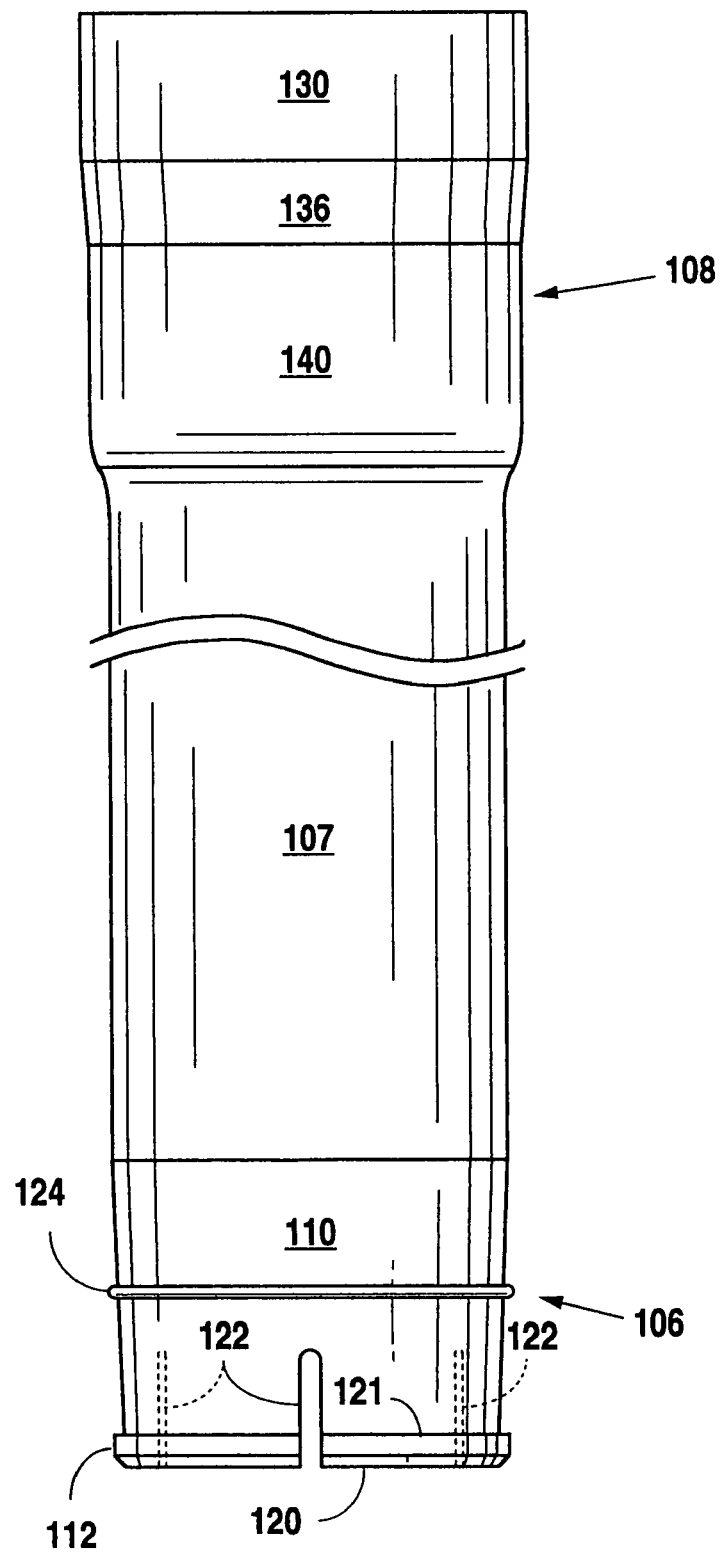
FIG. 2 is a side view of a length of the water well casing of the present invention casing showing the male and female ends.
Figure 3:
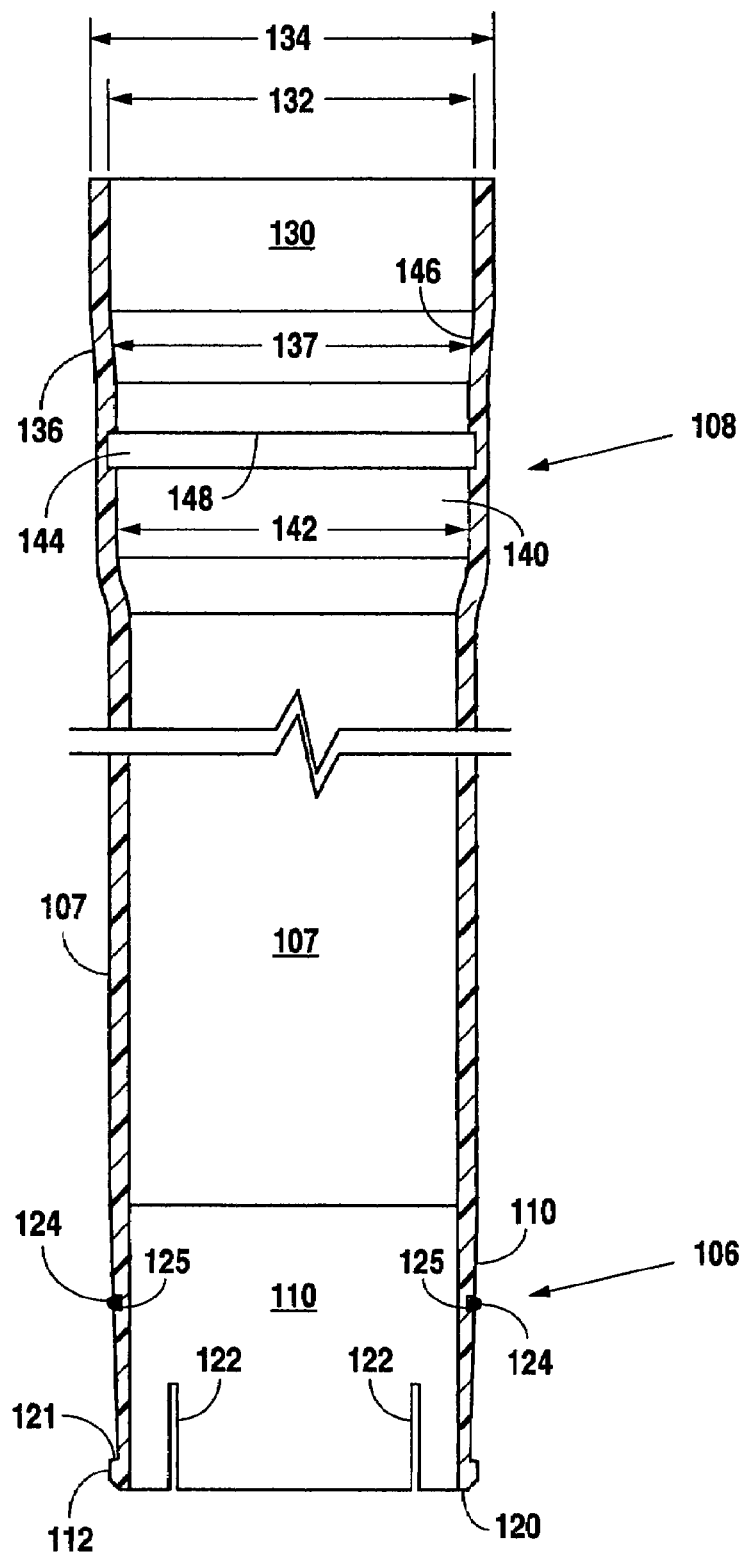
FIG. 3 is a cross-section view of FIG. 2.
Figure 4:
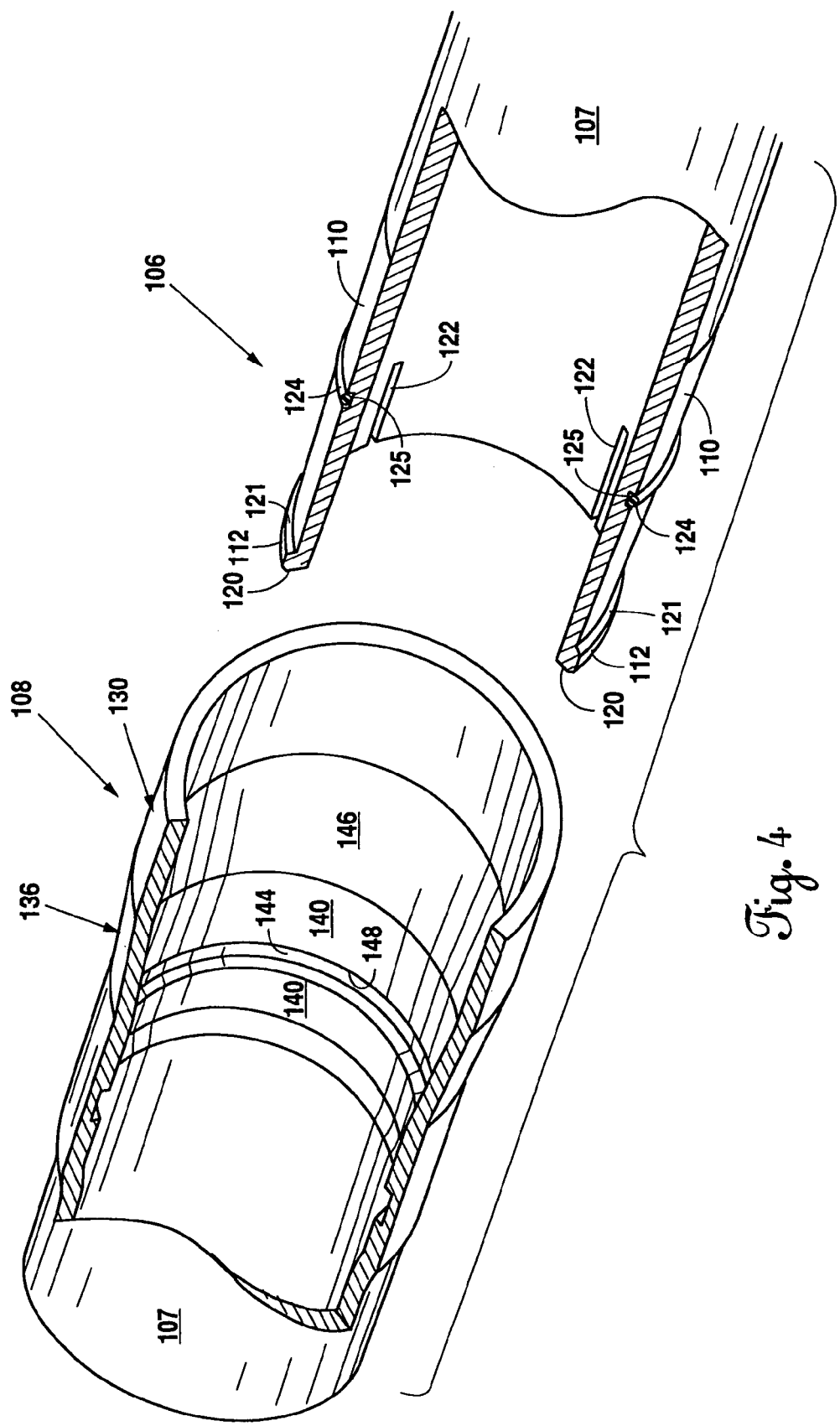
FIG. 4 is a perspective cutaway view of the male end and female end of the present invention.

FIGS. 2 and 3 show a side view and cross sectional view of the female end 108 of the water well casing 102 of the present invention while FIG. 4 illustrates a cutaway view. As shown in these views, the female end 108 has varying interior diameter which is wider at its outermost end. A first female section 130 is located at the outermost end of female end 108. The first female section 130 has a widened interior diameter 132 sufficient to receive the male end 106 and lip 112 of a similar casing with minimal clearance.

In the preferred embodiment, the length of the first female section 130 is sufficient to allow the first female section 130 to act as an alignment sleeve for the male end 106 of a similar casing. However, it is anticipated that the first female section 130 could be of varying lengths or have no length and only be the mouth of the female end 108. Also, in the preferred embodiment, the thickness of the wall of the first female section 130 is substantially equal to the thickness of the wall of the main length 107, such that, the outer diameter 134 of the first female section 130 is also widened. However, it is anticipated that the thickness of the first female section 130 and thus, its outer diameter 134 could vary.

Still referring to FIGS. 2, 3, and 4, a second female section 136 extends inwardly from the first female section 130. The second female section 136 has a tapering interior diameter 137 which narrows from the widened interior diameter 132 of the first female section 130 to a diameter which is less than the outer diameter of the lip 112 at the leading edge of the male end 106. In the preferred embodiment, the thickness of the wall of the second female section 136 is substantially equal to the thickness of the wall of the main length 107, such that, the outer diameter of the second female section 136 also tapers and narrows. However, it is anticipated that the thickness of the second female section 136 and thus, its outer diameter could vary.

Still referring to FIGS. 2, 3, and 4, a third female section 140 extends inwardly from the inner most end of the second female section 136 and has an interior diameter 142 which is substantially equal to the narrowest diameter of the tapering second female section 136. In the preferred embodiment, the thickness of the wall of the third female section 140 is substantially equal to the thickness of the wall of the main length 107. However, it is anticipated that the thickness of the third female section 140, and thus, its outer diameter could vary.

Figure 5:
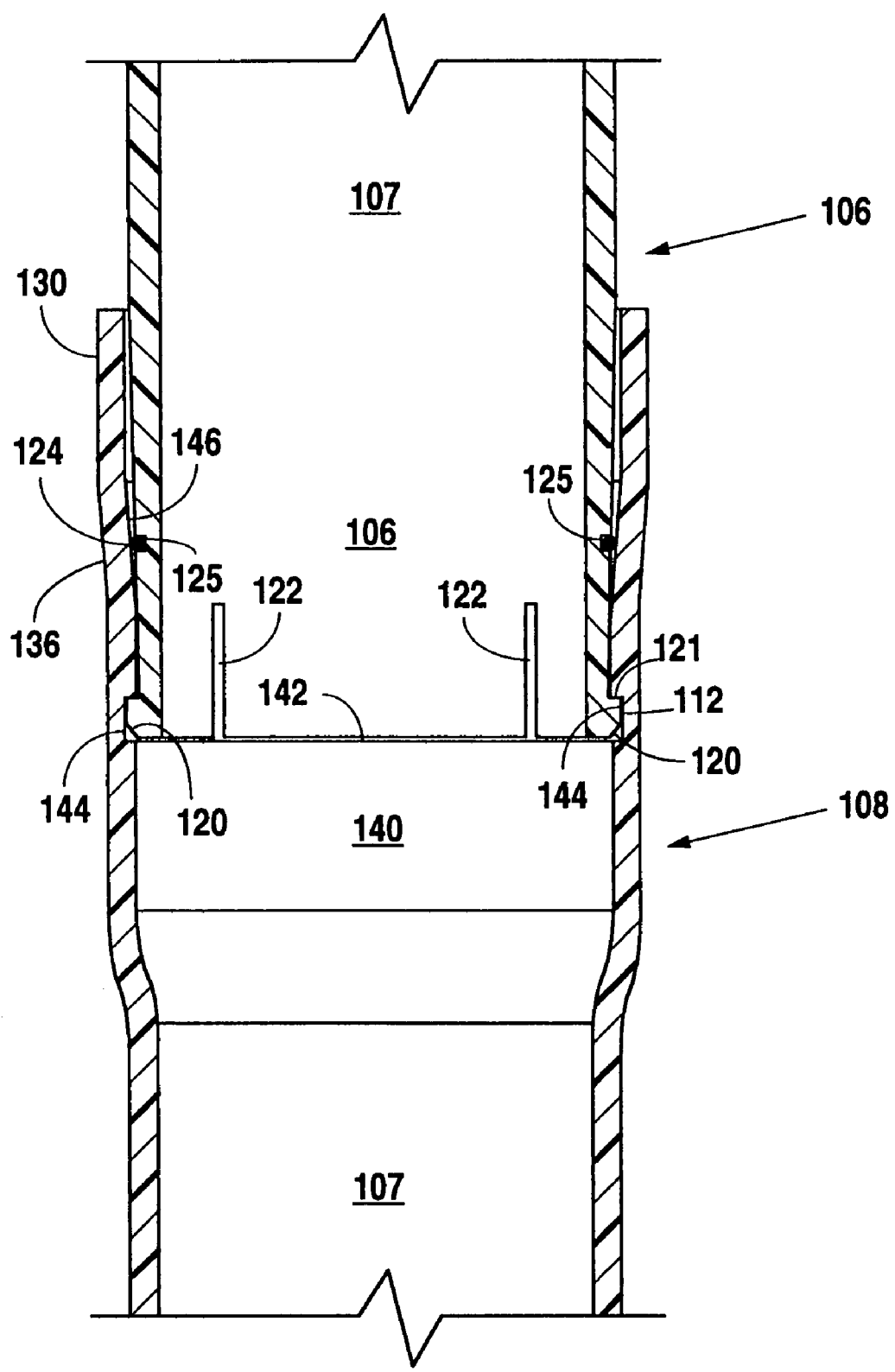
FIG. 5 is a cross-section view of FIG. 1 along cutting plane 5-5 of male end and female end.

Referring to FIGS. 3, 4, and 5, a circumferential groove 144 is cut into the interior surface of the female end 108. The groove 144 is of sufficient width and depth to receive the lip 112 at the leading edge of the male end 106 of a similar casing. In the preferred embodiment, the groove is positioned in the third female section 140. However, it is anticipated that the groove could also be positioned in the second female section 136.

As shown in FIGS. 2, 3, 4, and 5, an O-ring 124 is placed around the circumference of and engages the male end 106 of the casing 102. In the preferred embodiment, the O-ring rests within a groove 125 cut into the outer surface of the male end 106 around its circumference. However, it is anticipated that other placements of the O-ring could be utilized.

FIG. 4 depicts the general placement of a male end 106 and a female end 108 prior to insertion of male end 106 into female end 108. FIG. 5 is a cross-section view of the water well casing 102 with the male end 106 fully inserted into the female end 108.

Referring to FIGS. 4 and 5, in the preferred embodiment, as the male end 106 of casing 102 is inserted into the female end 108, the outer diameter of the lip 112 at the male end 106 makes contact with the interior surface 146 of the tapered second female section 136. As the male end 106 is further inserted, the interior surface 146 of the second female section 136 exerts a compressive force onto the lip 112 resulting in compression of the male end 106 with narrowing of the slots 122. At full insertion of the male end 106 into the female end 108, the lip 112 reaches groove 144 of female end 108, the compressive force on the lip 112 is released and the lip 112 expands into groove 144. The squared shoulder 121 engages the front wall 148 of the groove 144 locking the male end 106 of the lip 112 into female end 108. The engagement of the squared shoulder 121 of the lip 112 with the front wall 148 of the groove 144 resists pulling forces and prevents the connected casing 102 from being pulled apart under the hanging loads which exist when the casing 102 is placed in the water well. In addition, at full insertion, the O-ring 124 on male end 106 makes contact with the interior surface of female end 108, creating a seal.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A well casing length for connection to a similar well casing length comprising:
    a substantially cylindrical main length extending between a substantially cylindrical male end and a substantially cylindrical female end;
    a protrusion extending radially outwardly from the leading edge of said male end;
    said male end having a compressible circumference;
    a first section of said female end having a diameter sufficient to receive a male end and a protrusion of a similar well casing length therethrough;
    a second section of said female end having a diameter that is smaller than the diameter of said first section such that said second section will compress the circumference of a male end of a similar well casing length when a male end of a similar well casing length is inserted through said second section;
    a connection means for securing and holding the male end of said similar well casing length within the female end of said casing length.

2. The well casing length recited in claim 1 further comprising at least one slot through said male end extending from said leading edge.

3. The well casing length recited in claim 2 wherein said at least one slot is a plurality of slots.

4. The well casing length recited in claim 3 wherein said plurality of slots are evenly spaced around the circumference of said male end.

5. The well casing length recited in claim 1 where said protrusion is a lip around a substantial portion of the circumference of said male end.

6. The well casing length recited in claims 1 or 5 wherein said connection means is a first groove on the interior surface of said female end positioned to receive a protrusion extending radially outwardly from the leading edge of the male end of a similar length of well casing.

7. The well casing length recited in claim 6 wherein said first groove is recessed in the interior surface of said female end.

8. The well casing length recited in claim 7 wherein said first groove extends around a substantial portion of the interior circumference of said female end.

9. The well casing length recited in claims 1 or 5 wherein said connection means is a shoulder on the interior surface of said female end which abuts a shoulder formed by a protrusion extending radially outwardly from the leading edge of a male end of a similar length of well casing.

10. The well casing length recited in claim 9 where said shoulder extends around a substantial portion of the interior circumference of said female end.

11. The well casing length recited in claim 9 further comprising a second groove recessed in the outer surface of said male end positioned to receive an o-ring therein.

12. The well casing length recited in claim 1 further comprising an o-ring around the circumference of said male end.

13. The well casing length recited in claim 1 wherein the exterior diameter of said male end tapers from said main length to said protrusion.

14. A single length of well casing for attachment to another similar single length of well casing comprising:
 a substantially cylindrical main length extending between a substantially cylindrical male end and a substantially cylindrical female end;
 a protrusion extending radially outward from said male end;
 a first section of said female end having an interior diameter sufficient to receive a male end and a protrusion of a similar well casing length therethrough;
 a second section of said female end having an interior diameter that is smaller than the interior diameter of said first section such that said second section will compress the circumference of a male end of a similar well casing length when a male end of a similar well casing length is inserted through said second section;
 a groove recessed in the interior surface of said female end and positioned to receive a protrusion extending radially outwardly from the leading edge of a male end of a similar length of well casing.

15. The single length of well casing for attachment to another similar single length of well casing as recited in claim 14 wherein said protrusion extends from the leading edge of the male end.

16. The single length of well casing for attachment to another similar single length of well casing as recited in claim 14 wherein said interior diameter of said second section tapers from a larger diameter to a smaller diameter.

17. The single length of well casing for attachment to another similar single length of well casing as recited in claim 14 further comprising at least one slot through said male end extending from said leading edge.

18. The single length of well casing for attachment to another similar single length of well casing as recited in claim 17 wherein said at least one slot is a plurality of slots.

19. The single length of well casing for attachment to another similar single length of well casing as recited in claim 18 wherein said plurality of slots are evenly spaced around the circumference of said male end.

20. The single length of well casing for attachment to another similar single length of well casing as recited in claim 14 wherein the exterior diameter of said male end tapers from said main length to said protrusion.

21. The single length of well casing for attachment to another similar single length of well casing as recited in claim 14 wherein said groove secures and holds said male end of said similar length of well casing within said female end.

22. The single length of well casing for attachment to another similar single length of well casing as recited in claim 21 wherein said groove extends around a substantial portion of the interior circumference of said female end.

23. A single length of well casing for attachment to another similar single length of well casing comprising:
 a substantially cylindrical main length extending between a substantially cylindrical male end and a substantially cylindrical female end;
 a protrusion extending radially outward from said male end;
 a first section of said female end having an interior diameter sufficient to receive a male end and a protrusion of a similar well casing length therethrough;
 a second section of said female end having an interior diameter that is smaller than the interior diameter of said first section such that said second section will compress the circumference of a male end of a similar well casing length when a male end of a similar well casing length is inserted through said second section;
 a shoulder on the interior surface of said female end for engagement with a shoulder formed by a protrusion extending radially outwardly from the leading edge of a male end of a similar length of well casing.

24. The single length of well casing for attachment to another similar single length of well casing as recited in claim 23 wherein said protrusion extends from the leading edge of the male end.

25. The single length of well casing for attachment to another similar single length of well casing as recited in claim 23 wherein said interior diameter of said second section tapers from a larger diameter to a smaller diameter.

26. The single length of well casing for attachment to another similar single length of well casing as recited in claim 23 further comprising at least one slot through said male end extending from said leading edge.

27. The single length of well casing for attachment to another similar single length of well casing as recited in claim 26 wherein said at least one slot is a plurality of slots.

28. The single length of well casing for attachment to another single length of well casing as recited in claim 27 wherein said plurality of slots are evenly spaced around the circumference of said male end.

29. The single length of well casing for attachment to another single length of well casing as recited in claim 23 wherein the exterior diameter of said male end tapers from said main length to said protrusion.

30. A single length of polyvinyl chloride (PVC) well casing for attachment to another single length of polyvinyl chloride (PVC) well casing comprising:
 a substantially cylindrical main length extending between a substantially cylindrical male end and a substantially cylindrical female end;
 a protrusion extending radially outward from said male end;
 a first section of said female end having an interior diameter sufficient to receive a male end and a protrusion of a similar well casing length therethrough;
 a second section of said female end having an interior diameter that is smaller than the interior diameter of said first section such that said second section will compress the circumference of a male end of a similar well casing length when a male end of a similar well casing length is inserted through said second section;

a groove recessed in the interior surface of said female end positioned to receive a protrusion extending radially outwardly from the leading edge of a male end of a similar length of well casing.

31. The single length of polyvinyl chloride (PVC) well casing for attachment to another similar single length of polyvinyl chloride (PVC) well casing as recited in claim 30 wherein said protrusion extends from the leading edge of the male end.

32. The single length of polyvinyl chloride (PVC) well casing for attachment to another similar single length of polyvinyl chloride (PVC) well casing as recited in claim 30 wherein said interior diameter of said second section tapers from a larger diameter to a smaller diameter.

33. The single length of polyvinyl chloride (PVC) well casing for attachment to another similar single length of polyvinyl chloride (PVC) well casing as recited in claim 30 further comprising at least one slot through said male end extending from said leading edge.

34. The single length of polyvinyl chloride (PVC) well casing for attachment to another similar single length of polyvinyl chloride (PVC) well casing as recited in claim 33 wherein said at least one slot is a plurality of slots.

35. The single length of polyvinyl chloride (PVC) well casing for attachment to another similar single length of polyvinyl chloride (PVC) well casing as recited in claim 34 wherein said plurality of slots are evenly spaced around the circumference of said male end.

36. The single length of polyvinyl chloride (PVC) well casing for attachment to another similar single length of polyvinyl chloride (PVC) well casing as recited in claim 30 wherein the exterior diameter of said male end tapers from said main length to said protrusion.

37. The single length of polyvinyl chloride (PVC) well casing for attachment to another similar single length of polyvinyl chloride (PVC) well casing as recited in claim 30 wherein said groove secures and holds said male end of said similar length of well casing within said female end.

38. The single length of polyvinyl chloride (PVC) well casing for attachment to another similar single length of polyvinyl chloride (PVC) well casing as recited in claim 37 wherein said groove extends around a substantial portion of the interior circumference of said female end.

39. A single length of polyvinyl chloride (PVC) well casing for attachment to another similar single length of polyvinyl chloride (PVC) well casing comprising:

a substantially cylindrical main length extending between a substantially cylindrical male end and a substantially cylindrical female end;

a protrusion extending radially outward from said male end;

a first section of said female end having an interior diameter sufficient to receive a male end and a protrusion of a similar well casing length therethrough;

a second section of said female end having an interior diameter that is smaller than the interior diameter of said first section such that said second section will compress the circumference of a male end of a similar well casing length when a male end of a similar well casing length is inserted through said second section;

a shoulder on the interior surface of said female end for engagement with a shoulder formed by 1 protrusion extending radially outwardly from the leading edge of a male end of a similar length of well casing.

40. The single length of polyvinyl chloride (PVC) well casing for attachment to another single length of polyvinyl chloride (PVC) well casing as recited in claim 39 wherein said protrusion extends from the leading edge of the male end.

41. The single length of polyvinyl chloride (PVC) well casing for attachment to another single length of polyvinyl chloride (PVC) well casing as recited in claim 39 wherein said interior diameter of said second section tapers from a larger diameter to a smaller diameter.

42. The single length of polyvinyl chloride (PVC) well casing for attachment to another similar single length of polyvinyl chloride (PVC) well casing as recited in claim 39 further comprising at least one slot through said male end extending from said leading edge.

43. The single length of polyvinyl chloride (PVC) well casing for attachment to another similar single length of polyvinyl chloride (PVC) well casing as recited in claim 42 wherein said at least one slot is a plurality of slots.

44. The single length of polyvinyl chloride (PVC) well casing for attachment to another similar single length of polyvinyl chloride (PVC) well casing as recited in claim 43 wherein said plurality of slots are evenly spaced around the circumference of said male end.

45. The single length of polyvinyl chloride (PVC) well casing for attachment to another similar single length of polyvinyl chloride (PVC) well casing as recited in claim 39 wherein the exterior diameter of said male end tapers from said main length to said protrusion.

* * * * *